US010624908B2

(12) United States Patent
Kosec et al.

(10) Patent No.: US 10,624,908 B2
(45) Date of Patent: *Apr. 21, 2020

(54) PHOSPHOPANTETHEINE COMPOUNDS ALONE OR IN COMBINATION WITH HMG-COA REDUCTASE INHIBITORS FOR LOWERING SERUM CHOLESTEROL AND SERUM TRIGLICERIDES

(71) Applicants: COMET THERAPEUTICS, INC., Cambridge, MA (US); RIJKSUNIVERSITEIT GRONINGEN, Groningen (NL); ACADEMISCH ZIEKENHUIS GRONINGEN, Groningen (NL)

(72) Inventors: Gregor Kosec, Ljubljana (SI); Stefan Fujs, Ljubljana (SI); Hrvoje Petkovic, Ljubljana (SI); Oda Cornelia Maria Sibon, Groningen (NL); Balaji Srinivasan, Groningen (NL)

(73) Assignees: COMET THERAPEUTICS, INC., Cambridge, MA (US); RIJKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/539,340

(22) PCT Filed: Dec. 23, 2015

(86) PCT No.: PCT/EP2015/081184
§ 371 (c)(1),
(2) Date: Jun. 23, 2017

(87) PCT Pub. No.: WO2016/102680
PCT Pub. Date: Jun. 30, 2016

(65) Prior Publication Data
US 2018/0214461 A1 Aug. 2, 2018

(30) Foreign Application Priority Data
Dec. 23, 2014 (SI) .................. P-201400452

(51) Int. Cl.
*A61K 31/661* (2006.01)
*A61K 31/345* (2006.01)
*A61P 3/06* (2006.01)
*A61K 31/40* (2006.01)

(52) U.S. Cl.
CPC .......... *A61K 31/661* (2013.01); *A61K 31/345* (2013.01); *A61K 31/40* (2013.01); *A61P 3/06* (2018.01)

(58) Field of Classification Search
USPC ........................................................ 514/119
See application file for complete search history.

(56) References Cited

FOREIGN PATENT DOCUMENTS

| EP | 2 476 408 A1 | 7/2012 |
|---|---|---|
| WO | WO 2004/004774 A2 | 1/2004 |
| WO | WO 2014/011676 A1 | 1/2014 |
| WO | WO 2015/063177 A1 | 5/2015 |

OTHER PUBLICATIONS

Chen et al., "The Effects of Coenzyme A on Serum Lipids in Patients With Hyperlipidemia: Results of a Multicenter Clinical Trial", *J Clin Endocrinol Metab*, 2013, vol. 98, No. 2, p. E275-E278.
Database Caplus, Chemical Abstracts Service Database accession No. 1980:488844, "Stimulation of fatty acid metabolism by pantethine", entered May 12, 1984, 2 pages.
Lai, J. et al. "Efficacy and tolerability of adding coenzyme a 400 U/d capsule to stable statin therapy for the treatment of patients with mixed dyslipidemia: an 8-week, multicenter, double-Blind, randomized, placebo-controlled study", *Lipids in Health and Disease*, 2014, Vol . 13, No. 1, p. 1.
Nishimura et al., "Production of Coenzyme A by Sarcina lutea", *Applied Microbiology*, 1974, vol. 28, No. 1, p. 117-123.
Rothmann, M. et al. "Metabolic Perturbation of an Essential Pathway: Evaluation of a Glycine Precursor of Coenzyme A", *Journal of the American Chemical Society*, 2013, vol. 135, No. 16, pp. 5962-5965.
Shimizu et al., "Production of Coenzyme A by a Mutant of Brevibacterium ammoniagenes Resistant to Oxypantetheine", *Applied and Environmental Microbiology*, 1984, vol. 48, No. 6, p. 1118-1122.
Kameda, Kin-ya et al. "Stimulation of fatty acid metabolism by pantethine", Natural Sulfur Compounds, Laboratory of Biochemistry, Research Institute Daiichi Seiyaku Co., Ltd., Tokyo Japan, 1979, p. 443-452.

*Primary Examiner* — Kathrien A Cruz
(74) *Attorney, Agent, or Firm* — Cooley LLP; Heidi A. Erlacher; Xixi Sun (57) ABSTRACT

The invention relates to the use of phosphopantetheine compounds alone and in combination with 3-hydroxy-3-methylglutaryl-coenzyme A reductase inhibitors. Preferred medical uses relate to the treatment or prevention of dyslipidemia.

18 Claims, 2 Drawing Sheets

PHOSPHOPANTETHEINE COMPOUNDS ALONE OR IN COMBINATION WITH HMG-COA REDUCTASE INHIBITORS FOR LOWERING SERUM CHOLESTEROL AND SERUM TRIGLICERIDES

RELATED APPLICATIONS

This application is a U.S. National Phase application, filed under 35 U.S.C. § 371(c), of International Application No. PCT/EP2015/081184, filed Dec. 23, 2015, which claims the benefit of and priority to Slovenian Patent Application No. P-201400452, filed Dec. 23, 2014. The entire contents of each of these Applications are incorporated herein by reference in their entireties.

FIELD OF THE INVENTION

The present invention relates to the use of phosphopantetheine compounds for treatment or prevention of dyslipidemia. This invention also relates to combinations of 3-hydroxy-3-methylglutaryl-coenzyme A reductase inhibitors and phosphopantetheine compounds and medical uses thereof.

BACKGROUND OF THE INVENTION

HMG-CoA reductase or 3-hydroxy-3-methyl-glutaryl-CoA reductase is the rate-controlling enzyme of the mevalonate pathway, the metabolic pathway that produces cholesterol and other isoprenoids. Competitive inhibitors of HMG-CoA reductase increase the expression of low density lipoprotein (LDL) receptors in the liver, which in turn increases the catabolism of plasma LDL and decreases the plasma concentration of cholesterol, an important determinant of atherosclerosis. Therefore, HMG-CoA reductase has therefore been a target for pharmaceutical intervention, resulting in a group of widely available cholesterol-lowering drugs known collectively as the statins. These drugs include for example of lovastatin, simvastatin, pravastatin, fluvastatin, atorvastatin, cerivastatin, mevastatin and rosuvastatin. However, despite increasing use of statins, even in optimal doses to achieve target LDL-cholesterol reduction, considerable residual risk remains. Such risk resides in elevated levels of triglycerides (TG), and subnormal levels of artheroprotective high-density lipoprotein cholesterol (HDL-cholesterol) [Lai et al. Lipids in Health and Disease, 2014, 13:1].

The metabolic cofactor coenzyme A (CoA) is an acyl group carrier involved in the oxidative catabolism of fatty acids as well as in transferring fatty acids from the cytoplasm to mitochondria. CoA is essential for over 100 metabolic reactions, and it has been estimated that CoA is an obligatory cofactor for 4% of known enzymatic reactions. Eukaryotic cells are believed to obtain this essential cofactor via an intracellular de novo biosynthetic route. This canonical pathway starts with the uptake of extracellular vitamin B5, which is converted via five conserved enzymatic reactions into intracellular Coenzyme A. These enzymes are, in order, pantothenate kinase, phosphopantothenoyl cysteine synthetase, phospho-N-pantothenoylcysteine decarboxylase, phosphopantetheine adenylyltransferase and dephospho-CoA kinase.

Administering patients with moderate dyslipidemia with CoA was shown to effectively reduce plasma triglyceride levels [Chen et al., J Clin Enocrinol Metab, 2013, 98: E275-E278]. It has been described that combinations of statins and Coenzyme A in patients with hypercholesterolemia and hypertriglyceridemia, improved triglyceride levels and other lipoprotein parameters to a greater extent than statin alone [Lai et al. Lipids in Health and Disease, 2014, 13:1]. Similar combinations have also been shown effective in reducing plasma lipid levels rabbits and rats [Na et al., Academic Journal of Second Military Medical University, 2004, 25:255-257]. However, due to its complex chemical structure Coenzyme A is not readily available in industrial amounts through chemical synthesis. Coenzyme A from microbial sources, can be obtained, however yields are relatively low and isolation complex [Nishimura et al., Appl Microbiol. 1974, 28:117-23; Shimizu et al., Appl Environ Microbiol. 1984, 48:1118-22], therefore coenzyme A is not widely available in pure form.

SUMMARY OF THE INVENTION

Against this background, it is an object of the invention to provide novel pharmaceutical compositions useful for treating dyslipidemia, such as hyperlipidemia, hypercholesterolemia, hyperlipoproteinemia and hypertriglyceridemia and particularly combined hyperlipidemia. It is another object of the invention to provide novel pharmaceutical compositions useful for treating dyslipidemia, which pharmaceutical compositions are more effective in treating the disease. It is another object of the invention to provide novel pharmaceutical compositions useful for treating dyslipidemia, which pharmaceutical compositions comprise a phosphopantetheine compound. It is another object of the invention to provide novel pharmaceutical compositions useful for treating dyslipidemia, which pharmaceutical compositions have less side effects, e.g., show decreased toxicity, when treating the disease. It is further an object of the invention to provide novel pharmaceutical compositions useful for treating dyslipidemia, which pharmaceutical compositions comprise compounds which are more stable in human serum. The present invention also relates to treatment methods using pharmaceutical compositions of the invention, and to medicaments useful in treating dyslipidemia.

One aspect of the invention relates to a compound having a structural formula:

(Structure I)

wherein:
$R_a$ is H, preferably and; wherein:
$R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_{11}$, —$C(O)OR_{11}$, —$C(O)NR_{11}R_{12}$, —$C$=$NR_{11}$, —CN, —$OR_{11}$, —$OC(O)R_{11}$, —$NR_{11}R_{12}$, —$NR_{11}C(O)R_{12}$, —$NO_2$, —$N$=$CR_{11}R_{12}$ or -halogen; preferably $C_1$-$C_{10}$ alkyl, more preferably -methyl, -ethyl, -propyl or -butyl, such as t-butyl, most preferred -methyl;

$R_2$, $R_3$, Rb and Rc are independently selected from the group consisting of: —H, -methyl, -ethyl, -phenyl, acetoxymethyl (AM), pivaloyloxymethyl (POM), or
$R_2$ and $R_3$ or Rb and Rc jointly form a structure selected from the group consisting of:

wherein
$R_4$ is —H or -alkyl, preferably -methyl;
$R_5$ is —H or -alkyl, preferably -methyl or t-butyl;
$R_6$ is —H, -alkyl, or —$CH_2(CO)OCH_3$;
$R_7$ is —H, -alkyl or -halogen;

$R_8$ is —H, -alkyl, preferably t-butyl;
$R_9$ is —H, -alkyl, preferably -methyl or t-butyl;
$R_{10}$ is —H, -alkyl, preferably -methyl or t-butyl;
$R_{11}$ and $R_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt or solvate thereof for use in the treatment or prevention of dyslipidemia, hyperlipidemia, elevated blood cholesterol, elevated blood triglicerides, combined hyperlipidemia, artherosclerosis, cardiovascular disease, heart attack or stroke; preferably elevated blood cholesterol, elevated blood triglicerides, combined hyperlipidemia, artherosclerosis or cardiovascular disease; more preferably elevated blood cholesterol, elevated blood triglicerides or combined hyperlipidemia. In particularly preferred embodiments, said compound is useful for treating or preventing combined hyperlipidemia.

Preferred alkyl groups in the above definitions are -methyl, -ethyl, -propyl, -butyl, preferably t-butyl.

The D stereoisomeric configuration of carbon atoms marked with "*" is generally preferred.

In structures of the invention, a straight line overlayed by a wavy line denotes the covalent bond of the respective residue to the Structure I.

In preferred embodiments, $R_a$, $R_2$ and $R_3$ are H (4'-phosphopantetheine).

In preferred embodiments, R2, R3, Rb and Rc are identical residues. —H, bis-POM and bis-AM structures are particularly preferred.

In particularly preferred embodiments of any aspect of the invention, $R_2$, $R_3$, Rb and Rc are all ethyl or all -phenyl. In other preferred embodiments, $R_2$ and Rb are -ethyl and $R_3$ and Rc are -phenyl, or $R_3$ and Rc are -ethyl and $R_2$ and Rb are -phenyl.

In a second preferred embodiment, $R_2$, $R_3$, Rb and Rc are all where $R_4$ is —H, methyl; $R_5$ is alkyl, such as methyl or t-butyl. Preferably $R_4$ is —H and $R_5$ is -methyl. Hence, $R_2$, $R_3$, Rb and Rc may all be acetoxymethyl (AM). In another embodiment $R_4$ is —H and $R_5$ is t-butyl. Hence, $R_2$, $R_3$, Rb and Rc may all be pivaloyloxymethyl (POM).

In a third preferred embodiment, $R_2$ and $R_3$ are both

(acetooxybenzyl)

In a fourth preferred embodiment, $R_2$, $R_3$, Rb and Rc are all wherein $R_6$ is —H, -alkyl or —CH$_2$(CO)OCH$_3$.

In a fifth preferred embodiment, the phosphate group forms a cyclic phosphate according to the following structure:

wherein $R_7$ is alkyl or halogen or the cyclic phosphate includes:

wherein $R_8$ is t-butyl.

In a sixth preferred embodiment, $R_2$ and $R_3$ are both S-[(2-hydroxyethyl)sulfidyl]-2-thioethyl (DTE), or wherein $R_9$ is alkyl, preferably -methyl, -ethyl, -propyl or -butyl, such as t-butyl.

In a seventh preferred embodiment, $R_2$, $R_3$, Rb and Rc are all S-acyl-2-thioethyl (SATE), or wherein $R_{10}$ is alkyl, preferably -methyl, -ethyl, -propyl or -butyl, such as t-butyl.

In another embodiment, the present invention relates to pharmaceutical compositions comprising an HMG-CoA reductase inhibitor and a phosphopantetheine compound or a pharmaceutically acceptable salt or solvate thereof and use of said pharmaceutical compositions for the treatment of dyslipidemia, such as hyperlipidemia and combined hyperlipidemia.

The present invention thus relates to a pharmaceutical composition comprising an HMG-CoA reductase inhibitor and a phosphopantetheine compound or a pharmaceutically acceptable salt or solvate thereof.

In preferred embodiments the HMG-CoA reductase inhibitor in the pharmaceutical composition according to this invention is selected from the group consisting of lovastatin, simvastatin, pravastatin, fluvastatin, atorvastatin, cerivastatin, mevastatin, rosuvastatin, preferably atorvastatin and rosuvastatin, more preferably atorvastatin.

Therefore, in one aspect this invention relates to pharmaceutical composition comprising an HMG-CoA reductase inhibitor and a phosphopantetheine compound wherein said phosphopantetheine compound corresponds to the chemical formula

(Structure I)

wherein:

Ra is H, preferably and; wherein:

$R_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —COR$_{11}$, —C(O)OR$_{11}$, —C(O)NR$_{11}$R$_{12}$, —C=NR$_{11}$, —CN, —OR$_{11}$, —OC(O)R$_{11}$, —NR$_{11}$R$_{12}$, —NR$_{11}$C(O)R$_{12}$, —NO$_2$, —N=CR$_{11}$R$_{12}$ or -halogen; preferably C$_1$-C$_{10}$ alkyl, more preferably -methyl, -ethyl, -propyl or -butyl, such as t-butyl, most preferred -methyl;

$R_2$, $R_3$, Rb and Rc are independently selected from the group consisting of: —H, -methyl, -ethyl, -phenyl, acetoxymethyl (AM), pivaloyloxymethyl (POM), or
$R_2$ and $R_3$ or Rb and Rc jointly form a structure selected from the group consisting of:

wherein
$R_4$ is —H or -alkyl, preferably -methyl;
$R_5$ is —H or -alkyl, preferably -methyl or t-butyl;
$R_6$ is —H, -alkyl, or —$CH_2(CO)OCH_3$;
$R_7$ is —H, -alkyl or -halogen;
$R_8$ is —H, -alkyl, preferably t-butyl;
$R_9$ is —H, -alkyl, preferably -methyl or t-butyl;
$R_{10}$ is —H, -alkyl, preferably -methyl or t-butyl;
$R_{11}$ and $R_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;
or a pharmaceutically acceptable salt or solvate thereof.

Preferred alkyl groups in the above definitions are -methyl, -ethyl, -propyl, -butyl, preferably t-butyl.

The D stereoisomeric configuration of carbon atoms marked with "*" is generally preferred.

In structures of the invention, a straight line overlayed by a wavy line denotes the covalent bond of the respective residue to the Structure I.

In preferred embodiments, R2, R3, Rb and Rc are identical residues. —H, bis-POM and bis-AM structures are particularly preferred.

In particularly preferred embodiments of any aspect of the invention, $R_2$, $R_3$, Rb and Rc are all ethyl or all -phenyl. In other preferred embodiments, $R_2$ and Rb are -ethyl and $R_3$ and Rc are -phenyl, or $R_3$ and Rc are -ethyl and $R_2$ and Rb are -phenyl.

In a second preferred embodiment, $R_2$, $R_3$, Rb and Rc are all where $R_4$ is —H, methyl; $R_5$ is alkyl, such as methyl or t-butyl. Preferably $R_4$ is —H and $R_5$ is -methyl. Hence, $R_2$, $R_3$, Rb and Rc may all be acetoxymethyl (AM). In another embodiment $R_4$ is —H and $R_5$ is t-butyl. Hence, $R_2$, $R_3$, Rb and Rc may all be pivaloyloxymethyl (POM).

In a third preferred embodiment, $R_2$ and $R_3$ are both

(acetooxybenzyl)

In a fourth preferred embodiment, R2, R3, Rb and Rc are all wherein $R_6$ is —H, -alkyl or —$CH_2(CO)OCH_3$.

In a fifth preferred embodiment, the phosphate group forms a cyclic phosphate according to the following structure:

wherein $R_7$ is alkyl or halogen or the cyclic phosphate includes:

wherein $R_8$ is t-butyl.

In a sixth embodiment, $R_2$ and $R_3$ are both S-[(2-hydroxyethyl)sulfidyl]-2-thioethyl (DTE), or wherein $R_9$ is alkyl, preferably -methyl, -ethyl, -propyl or -butyl, such as t-butyl.

In a seventh preferred embodiment, $R_2$, $R_3$, Rb and Rc are all S-acyl-2-thioethyl (SATE), or wherein $R_{10}$ is alkyl, preferably -methyl, -ethyl, -propyl or -butyl, such as t-butyl.

Preferred alkyl groups are -methyl, -ethyl, -propyl, -butyl, preferably t-butyl.

The D stereoisomeric configuration of carbon atoms marked with "*" is generally preferred.

In preferred embodiments, said pharmaceutical composition is useful in the treatment or prevention of dyslipidemia, hyperlipidemia, elevated blood cholesterol, elevated blood triglicerides, combined hyperlipidemia, artherosclerosis, cardiovascular disease, heart attack or stroke; preferably elevated blood cholesterol, elevated blood triglicerides, combined hyperlipidemia, artherosclerosis or cardiovascular disease; more preferably elevated blood cholesterol, elevated blood triglicerides or combined hyperlipidemia. In particularly preferred embodiments, said pharmaceutical composition is useful in the treatment or prevention combined hyperlipidemia.

Hence, an aspect of the invention relates to a method for treating or preventing of dyslipidemia, hyperlipidemia, elevated blood cholesterol, elevated blood triglicerides, combined hyperlipidemia, artherosclerosis, cardiovascular disease, heart attack or stroke. Even more preferably the present invention relates to a method for the treatment or prevention of elevated blood cholesterol, elevated blood triglicerides, combined hyperlipidemia, artherosclerosis or cardiovascular disease. In more preferred embodiments the present invention relates to a method for the treatment or prevention of elevated blood cholesterol, elevated blood triglicerides or combined hyperlipidemia. In most preferred embodiments the present invention relates to a method for the treatment or prevention of combined hyperlipidemia.

In further embodiments, the present invention relates to the use of said pharmaceutical composition for treating or preventing elevated blood cholesterol in a mammal in need thereof comprising administering an HMG-CoA reductase inhibitor and a phosphopantetheine compound. Preferably, said mammal is a human.

In further embodiments, the present invention relates the use of said pharmaceutical composition for treating or preventing elevated blood cholesterol in a mammal in need thereof comprising sequentially administering a phosphopantetheine compound and an HMG-CoA reductase inhibitor. Preferably, said mammal is a human.

In further embodiments, the present invention relates the use of said pharmaceutical composition for treating or preventing artherosclerosis in a mammal in need thereof comprising administering a phosphopantetheine compound and an HMG-CoA reductase inhibitor. Preferably, said mammal is a human.

In further embodiments, the present invention relates the use of said pharmaceutical composition for treating or preventing cardiovascular disease in a mammal in need thereof comprising administering a phosphopantetheine compound and an HMG-CoA reductase inhibitor. Preferably, said mammal is a human.

In further embodiments, the present invention relates the use of said pharmaceutical composition for treating or preventing heart attack in a mammal in need thereof comprising administering a phosphopantetheine compound and an HMG-CoA reductase inhibitor. Preferably, said mammal is a human.

In further embodiments, the present invention relates the use of said pharmaceutical composition for treating or preventing stroke in a mammal in need thereof comprising administering a phosphopantetheine compound and an HMG-CoA reductase inhibitor. Preferably, said mammal is a human.

In further embodiments, the present invention relates the use of said pharmaceutical composition for treating or preventing combined hyperlipidemia in a mammal in need thereof comprising administering a phosphopantetheine compound and an HMG-CoA reductase inhibitor. Preferably, said mammal is a human.

In further embodiments, the present invention relates to the use of a composition in the manufacture of a medicament for treating or preventing elevated blood cholesterol in a mammal in need thereof, said composition comprising an HMG-Co A reductase inhibitor and a phosphopantetheine compound.

In yet another embodiment the present invention relates to a kit comprising in separate containers in a single package pharmaceutical compositions for use in combination which comprises in one container a pharmaceutical composition comprising an effective amount of a HMG-CoA reductase inhibitor in a pharmaceutically acceptable carrier, and in a second-container, a pharmaceutical composition comprising an effective amount of a phosphopantetheine compound.

DETAILED DESCRIPTION OF THE INVENTION

Within the context of the present invention the term "combined hyperlipidemia" refers to concurrent occurrence of hypercholesterolemia and hypertriglyceridemia.

The term "alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least two carbon atoms covalently connected by a double bond.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise defined, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3-to 15 membered ring radical which consists of carbon atoms and from one to five heteroatoms selected from the group consisting of nitrogen, oxygen, and sulfur, preferably a 4-to 8-membered ring with one or more heteroatoms, more preferably a 5- or 6-membered ring with one or more heteroatoms. It may be aromatic or not. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e. g., methoxy, ethoxy, propoxy, etc.

References herein to "substituted" groups in the compounds of the present invention refer to the specified moiety that is substituted at one or more available positions by one or more suitable groups, e. g., halogen such as fluoro, chloro, bromo and iodo, cyano, hydroxyl, nitro, azido, alkanoyl such as a C1-6 alkanoyl group such as acyl and the like, carboxamido, alkyl groups including those groups having 1 to about 12 carbon atoms or from 1 to about 6 carbon atoms and more preferably 1-3 carbon atoms, alkenyl and alkynyl groups including groups having one or more unsaturated linkages and from 2 to about 12 carbon or from 2 to about 6 carbon atoms, alkoxy groups having one or more oxygen linkages and from 1 to about 12 carbon atoms or 1 to about 6 carbon atoms, aryloxy such as phenoxy, alkylthio groups including those moieties having one or more thioether linkages and from 1 to about 12 carbon atoms or from 1 to about 6 carbon atoms, alkylsulfinyl groups including those moieties having one or more sulfinyl linkages and from 1 to about 12 carbon atoms or from 1 to about 6 carbon atoms, alkylsulfonyl groups including those moieties having one or more sulfonyl linkages and from 1 to about 12 carbon atoms or from 1 to about 6 carbon atoms, aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "pharmaceutically acceptable salts or solvates" refers to any pharmaceutically acceptable salt, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art. For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

The term "phosphopantetheine compound" refers to the chemical formula (Structure I)

wherein:
Ra is H,

-continued preferably and; wherein:

R$_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —COR$_{11}$, —C(O)OR$_{11}$, —C(O)NR$_{11}$R$_{12}$, —C=NR$_{11}$, —CN, —OR$_{11}$, —OC(O)R$_{11}$, —NR$_{11}$R$_{12}$, —NR$_{11}$C(O)R$_{12}$, —NO$_2$, —N=CR$_{11}$R$_{12}$ or -halogen; preferably C$_1$-C$_{10}$ alkyl, more preferably -methyl, -ethyl, -propyl or -butyl, such as t-butyl, most preferred -methyl;

R$_2$, R$_3$, Rb and Rc are independently selected from the group consisting of: —H, -methyl, -ethyl, -phenyl, acetoxymethyl (AM), pivaloyloxymethyl (POM), or R$_2$ and R$_3$ or Rb and Rc jointly form a structure selected from the group consisting of:

wherein

R$_4$ is —H or -alkyl, preferably -methyl;
R$_5$ is —H or -alkyl, preferably -methyl or t-butyl;
R$_6$ is —H, -alkyl, or —CH$_2$(CO)OCH$_3$;
R$_7$ is —H, -alkyl or -halogen;
R$_8$ is —H, -alkyl, preferably t-butyl;
R$_9$ is —H, -alkyl, preferably -methyl or t-butyl;
R$_{10}$ is —H, -alkyl, preferably -methyl or t-butyl;
R$_{11}$ and R$_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

Preferred alkyl groups in the above definitions are -methyl, -ethyl, -propyl, -butyl, preferably t-butyl.

The D stereoisomeric configuration of carbon atoms marked with "*" is generally preferred.

In structures of the invention, a straight line overlayed by a wavy line denotes the covalent bond of the respective residue to the Structure I.

In preferred embodiments, R$_a$, R$_2$ and R$_3$ are H (4'-phosphopantetheine).

In preferred embodiments, R2, R3, Rb and Rc are identical residues. —H, bis-POM and bis-AM structures are particularly preferred. In particularly preferred embodiments of any aspect of the invention, R$_2$, R$_3$, Rb and Rc are all ethyl or all -phenyl. In other preferred embodiments, R$_2$ and Rb are -ethyl and R$_3$ and Rc are -phenyl, or R$_3$ and Rc are -ethyl and R$_2$ and Rb are -phenyl.

In a second preferred embodiment, R$_2$, R$_3$, Rb and Rc are all where R$_4$ is —H, methyl; R$_5$ is alkyl, such as methyl or t-butyl. Preferably R$_4$ is —H and R$_5$ is -methyl. Hence, R$_2$, R$_3$, Rb and Rc may all be acetoxymethyl (AM). In another embodiment R$_4$ is —H and R$_5$ is t-butyl. Hence, R$_2$, R$_3$, Rb and Rc may all be pivaloyloxymethyl (POM).

In third preferred embodiment, R$_2$ and R$_3$ are both

(acetooxybenzyl)

In a fourth preferred embodiment, $R_2$, $R_3$, Rb and Rc are all wherein $R_6$ is —H, -alkyl or —$CH_2(CO)OCH_3$.

In fifth preferred embodiment, the phosphate group forms a cyclic phosphate according to the following structure:

wherein $R_7$ is alkyl or halogen or the cyclic phosphate includes:

wherein $R_8$ is t-butyl.

In sixth preferred embodiment, $R_2$ and $R_3$ are both S-[(2-hydroxyethyl)sulfidyl]-2-thioethyl (DTE), or wherein $R_9$ is alkyl, preferably -methyl, -ethyl, -propyl or -butyl, such as t-butyl.

In a seventh preferred embodiment, $R_2$, $R_3$, Rb and Rc are all S-acyl-2-thioethyl (SATE), or wherein $R_{10}$ is alkyl, preferably -methyl, -ethyl, -propyl or -butyl, such as t-butyl.

Pharmaceutical composition comprising a phosphopantetheine compound or a combination comprising an HMG-CoA reductase inhibitor and a phosphopantetheine compound is particularly suitable for treatment or prevention of hypercholesterolemia and hypertriglyceridemia which is herein referred to as "combined hyperlipidemia".

This invention is based on our new and surprising finding that in mammalian serum Coenzyme A is rapidly hydrolyzed, likely by ecto-nucleotide-pyrophosphatases to 4'-phosphopantetheine. Moreover we determined that 4'-phosphopantetheine is a biologically stable molecule that surprisingly is able to effectively translocate through cell membranes in spite of the charge present on the phosphate group. Inside the cell, 4'-phosphopantetheine is enzymatically converted to Coenzyme A by the bi-functional enzyme CoA synthase.

Up to now, the de novo biosynthetic pathway starting with the uptake of vitamin B5 was the only known route for cells and organisms to obtain CoA. This invention is based on our finding that extracellular sources of CoA influence intracellular CoA levels both in vitro and in vivo. Our results also show that CoA is not a biologically stable molecule and that cells do not absorb CoA directly. Surprisingly in fact, CoA in the serum is hydrolized into a stable product 4'-phosphopantetheine by ecto-nucleotide-pyrophosphatases. 4'-phosphopantetheine can then be taken up by cells and converted to CoA. Via this route, exogenous CoA rescues CoA-deprived phenotypes at the cellular, developmental, organismal and behavioral level. We prove that CoA-deprived phenotypes can also be rescued by 4'-phosphopantetheine, an intermediate in CoA biosynthetic pathway. This proves that CoA rescue is independent of the first three classic CoA biosynthetic steps (PANK, PPCS and PPCDC) and that it depends only on the last bifunctional enzyme COASY. Our data therefore demonstrate the existence of an previously unsuspected alternate mechanism for cells and organisms to influence intracellular CoA levels derived from an extracellular CoA source with 4'-phosphopantetheine as the key intermediate and hereby surprisingly demonstrating the high potential of 4'-phosphopantetheine.

Our findings have direct implications for the treatment or prevention of dyslipidemia, hyperlipidemia, elevated blood cholesterol, elevated blood triglycerides, combined hyperlipidemia, artherosclerosis, cardiovascular disease, heart attack or stroke. Patients suffering from hyperlipidemia were recently shown to benefit from a combined treatment of statins and 400 U Coenzyme A/day for 3 weeks [Lai et al. Lipids in Health and Disease, 2014, 13:1]. This combination was more effective compared to statins alone, demonstrating two things: CoA has an effect when orally provided; and no toxicity was observed following 3 weeks of administration. Based on our unsuspected findings that CoA is rapidly degraded to 4'-phosphopatetheine, these clinical data also imply a tolerance and efficacy for 4'-phosphopatetheine.

From the point of view of drug development we realized that 4'-phosphopantetheine has several important advantages compared to CoA. On one hand 4'-phosphopantetheine can be obtained by much simpler chemical synthesis procedure mastered by us and described in the patent application PCT/EP2014/073258 (published as WO2015/063177) which is herein incorporated in its entirety. More importantly, in contrast to chemically extremely complex CoA, derivatives of 4'-phosphopantetheine can be readily obtained resulting in compounds with advantageous pharmacological properties, as also described in PCT/EP2014/073258. Furthermore, 4'phosphopantetheine is a serum-stable compound in contrast to CoA. Also, 4'-phosphopantetheine is able to translocate through cell membranes in contrast to CoA.

Thus for treatment of dyslipidemia, hyperlipidemia, elevated blood cholesterol, elevated blood triglycerides, combined hyperlipidemia, artherosclerosis, cardiovascular disease, heart attack or stroke a pharmaceutical composition comprising a combination of a HMG-CoA reductase inhibitor and phosphopantetheine compound is clearly superior to the combination of HMG-CoA reductase inhibitor and CoA which was shown effective and safe before [Lai et al. Lipids in Health and Disease, 2014, 13:1]. Based on our results we claim in addition that phosphopantetheine compounds alone will be effective as treatment of dyslipidemia, hyperlipidemia, elevated blood cholesterol, elevated blood triglicerides, combined hyperlipidemia, artherosclerosis, cardiovascular disease, heart attack or stroke.

EXAMPLES

Example 1. Conversion of CoA into 4'-phosphopantetheine in Human Serum

Materials and Methods: CoA (purchased from Sigma) was incubated at a final concentration of 10 µM human serum for 6 hours at 37° C. After incubation, the samples were processed to remove proteins and HPLC analysis was used to assess the amount of remaining compound CoA and amount of generated 4'-phosphopantetheine, indicating conversion of CoA to 4'-phosphopantetheine.

Figure 1:
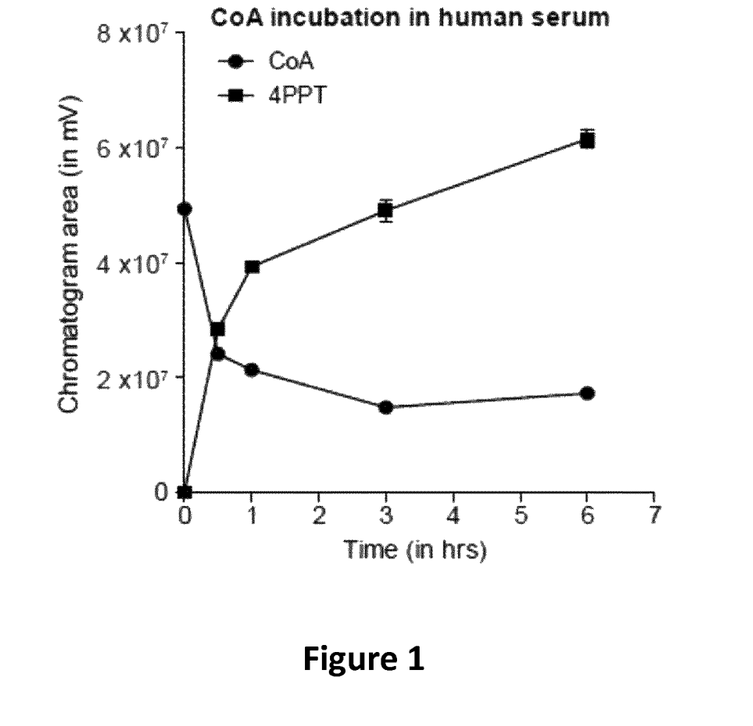
FIG. 1 shows the conversion of CoA into stable 4'-phosphopantetheine (4PPT) upon incubation of CoA in human serum. The graph shows relative levels determined by HPLC analysis of CoA and 4PPT in human serum over 6 hours incubation. It demonstrates that CoA is degraded in human serum and converted into stable 4PPT.

Results: CoA is significantly degraded (60%). already in 3 initial hours of incubation, most likely by ecto-nucleotide-pyrophosphatases. In parallel with CoA degradation the concentrations of 4'-phosphopantetheine were observed to increase confirming that CoA is converted into 4'-phosphopantetheine (FIG. 1).

Example 2: Rescue Potential of CoA and 4'-phosphopantetheine in HOPAN Assay

Mammalian HEK293 cells treated with the chemical inhibitor HOPAN (hopanthenate, CAS 17097-76-6, IUPAC: calcium 4-[[(2R)-2,4-dihydroxy-3,3-dimethylbutanoyl]amino]butanoate). Cells treated with HOPAN show a reduction in intracellular CoA levels, which induces a decrease in cell viability. Herewith, the result is included to demonstrate the rescue efficiency of CoA as well as 4'-phosphopantetheine in such model system.

Materials and Methods: HEK293 cells were cultured in vitamin B5 deficient DMEM (Thermo Scientific) supplemented with 10% dialysed FCS (Thermo Scientific) with and without HOPAN (0.5 mM) and CoA and 4'-phosphopantetheine for 4 days. 250 µM of CoA and 4'-phosphopantetheine was used for determination of rescue efficiency.

Figure 2:
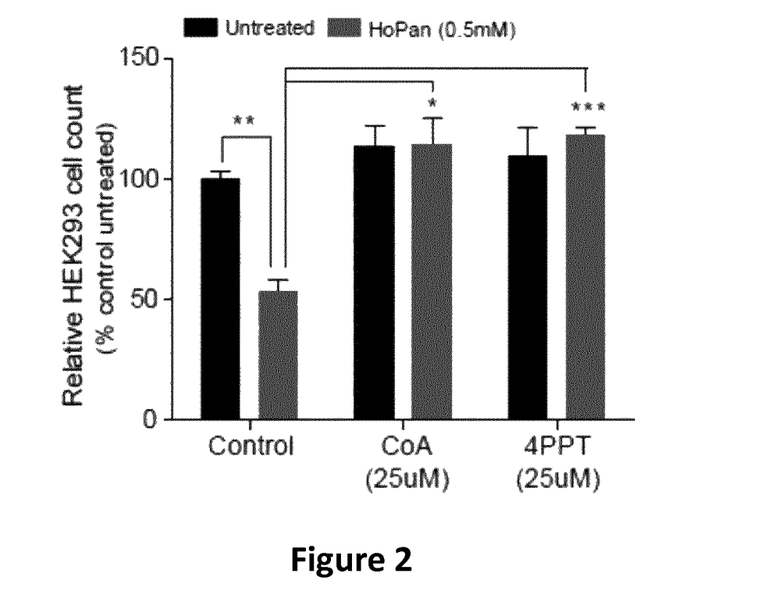
FIG. 2 shows the rescue potential of external supplementation of CoA or 4'-phosphopantetheine of a CoA-deprived phenotype in HoPan-(calcium 4-[[(2R)-2,4-dihydroxy-3,3-dimethylbutanoyl]amino]butanoate))-induced reduction of cell count in mammalian HEK293 cells. This novel result shows that 4PPT is as potent as CoA, this is because CoA is converted into 4PPT in serum
Figure 3:
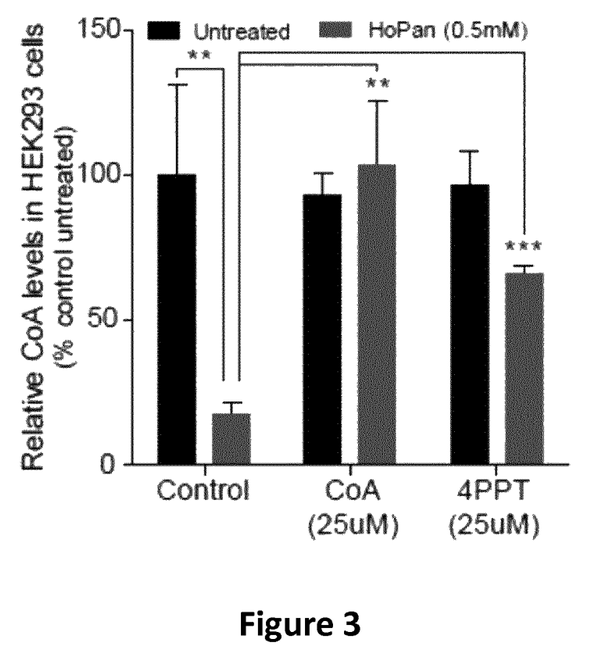
FIG. 3 shows the rescue potential of external supplementation of CoA or 4'-phosphopantetheine of a CoA-deprived phenotype in HoPan-(calcium 4-[[(2R)-2,4-dihydroxy-3,3-dimethylbutanoyl]amino]butanoate))-induced intracellular reduction of CoA levels in mammalian HEK293 cells. This novel result shows that 4PPT is as potent as CoA, this is because CoA is converted into 4PPT in serum.

Result: The result indicates that CoA and 4'-phosphopantetheine significantly rescued the HOPAN (0.5 mM) induced decrease of intracellular CoA levels (FIG. 3) and rescued the cell count defect (FIG. 2).

Example 3. Film Coated Tablets

The film-coated tablet is manufactured e.g. as follows:

A mixture of calcium salt of 4'-phosphopantetheine, calcium salt of atorvastatin, microcrystalline cellulose, crospovidone, part of the colloidal anhydrous silica/colloidal silicon dioxide/Aerosile 200, silicon dioxide and magnesium stearate is premixed in a diffusion mixer and then sieve through a screening mill. The resulting mixture is again premixed in a diffusion mixer, compacted in a roller compacter and then sieved through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tablets are coated with a film by using Diolack pale red in a perforated pan.

| Component | Composition per unit [mg] | Standards |
|---|---|---|
| 4'-phosphopantetheine, calcium salt | 300 | |
| Atorvastatin, calcium salt trihydrate | 21.7 | Ph. Eur |
| Microcristaline cellulose/Avicel PH 102 | 212 | Ph. Eur |
| Crospovidone | 80 | Ph. Eur |
| Colloidal anhydrous silica/Colloidal silicon dioxide/Aerosil 200 | 3.2 | Ph. Eur |
| Magnesium stearate | 100 | Ph. Eur |
| Blending | | |
| Colloidal anhydrous silica/Colloidal silicon dioxide/Aerosil 200 | 3.2 | Ph. Eur |
| Magnesium stearate | 80 | Ph. Eur |
| Coating | | |
| Purified water * | / | |
| DIOLACK pale red 00F34899 | 15 | |
| Total tablet mass | 815.1 | |

* Removed during processing

Example 4. Method for the Synthesis of 4'-phosphopantetheine (Corresponds to Example 9 of WO2015/063177)

D-Pantothenic acid was prepared from its hemicalcium salt (Aldrich, ≥99.0%) reacting with oxalic acid. S-Tritylcysteamine was synthesized from cysteamine hydrochloride and trityl chloride as reported by Mandel et al. [A. L. Mandel, et al., Org. Lett. 2004, 6, 26, 4801-4803]. Dibenzylchlorophosphate was prepared by reacting dibenzylphosphite with N-chlorosuccinimide as described by Itoh et al. [K. Itoh et al., Org. Lett. 2007, 9, 5, 879-882] in toluene as a solvent. All other chemicals were obtained from commercial sources and used without further purification; cysteamine hydrochloride (Aldrich, ≥98.0%), trityl chloride (Aldrich, 97.0%), N-(3-dimethylaminopropyl)-N'-ethylcarbodiimide (Aldrich, ≥97.0%), 1-hydroxybenzotriazole hydrate (Aldrich, ≥97.0%), dibenzylphosphite (Aldrich, technical grade), N-chlorosuccinimide (Aldrich, 98%). Column chromatography was carried out using Silica gel 60 Å, 60-100 mesh (Aldrich). Cation exchange chromatography was performed on DOWEX 50WX2, hydrogen form, 100-200 mesh (Aldrich). $^1$H and $^{13}$C NMR were recorded at 25° C. with Varian Unity Inova 300 MHz spectrometer (300 MHz/75 MHz). The chemical shifts (δ) are reported in ppm units relative to TMS as an internal standard where spectra recorded in $CDCl_3$ or relative to residual solvent signal when $D_2O$ was used. High-resolution mass spectra were obtained on AutospecQ mass spectrometer with negative electrospray ionization.

a) Coupling Reaction—Synthesis of S-tritylpantetheine

In dried acetonitrile (100 mL) were prepared separately: (A) D-pantothenic acid (2.19 g, 10.0 mmol), (B) S-tritylcysteamine (3.19 g, 10.0 mmol) and (C) N-(3-dimethylaminopropyl)-N'-ethylcarbodiimide (1.55 g, 10.0 mmol) together with 1-hydroxybenzotriazole hydrate (1.35 g, 10.0 mmol). When mixed together (A), (B) and (C), triethylamine (10.4 mL, 75 mmol) was added. The mixture was stirred at room temperature for 24 h and quenched with addition of water. The product was extracted with diethyl ether. The combined organic phases were washed with 1 M hydrochloric acid, saturated aqueous solution of NaHCO₃ and brine. Organic layer was dried over sodium sulfate and concentrated in vacuum to give S-tritylpantetheine (3.53 g, 68%) as pale-yellow crystals. $^1$H NMR (300 MHz, CDCl₃) δ 0.85 (s, 3H), 0.92 (s, 3H), 2.29 (t, J=6.2 Hz, 2H), 2.38 (t, J=6.4 Hz, 2H), 3.03 (dd, J=6.0, 5.2 Hz, 2H), 3.45 (m, 4H), 3.92 (s, 1H), 6.20 (t, J=5.7 Hz, 1H, NH), 7.21 (m, 3H), 7.27 (m, 6H), 7.39 (m, 6H).

b) Phosphorylation—Synthesis of S-trityl-4'-dibenzylphosphopantetheine

Dibenzylchlorophosphate was freshly prepared by reaction of dibenzylphosphite (2.16 g, 8.24 mmol) with N-chlorosuccinimide (1.21 g, 9.06 mmol) in toluene (40 mL) at room temperature for 2 h. The mixture was filtered and the filtrate was evaporated under vacuum and added to a solution of S-tritylpantetheine (2.86 g, 5.49 mmol), diisopropylethylamine (3.06 mL), 4-dimethylaminopyridine (0.067 g, 0.55 mmol) in dry acetonitrile. The mixture was stirred for 2 h at room temperature. Products were extracted into organic phase in dichloromethane—aqueous NaHCO₃ system. The organic extracts were washed with water and brine, and dried over Na₂SO₄. Evaporation of solvent gave a crude S-trityl-4'-dibenzylphosphopantetheine as a dark brown oil (4.69 g), which was further purified by flash chromatography to give a semicrystaline pale yellow product (0.640 g, 0.82 mmol). The yield of the synthesis and purification of S-trityl-4'-dibenzylphosphopantetheine is 15%. $^1$H NMR (300 MHz, CDCl₃) δ 0.75 (s, 3H), 1.03 (s, 3H), 2.32 (t, J=6.1 Hz, 2H), 2.4 (t, J=6.5 Hz, 2H), 3.06 (dd, J=6.5, 6.2 Hz, 2H), 3.47 (dd, J=6.1, 6.0 Hz, 2H), 3.60 (dd, J=9.9, 7.3 Hz 1H), 3.85 (s, 1H), 4.00 (dd, J=9.9, 7.0 Hz, 1H), 5.04 (m, 4H), 5.80 (t, J=5.5 Hz, 1H, NH), 7.18-7.42 (m, 25H).

c) Deprotection—Synthesis of 4'-phosphopantetheine

Naphthalene (12.9 g, 100.6 mmol) dissolved in tetrahydrofuran (70 mL) was added to sodium metal (2.21 g, 96.1 mmol) in tetrahydrofuran (50 mL). After 2 h the solution was cooled to −(35±5) °C. and S-trityl-4'-dibenzylphosphopantetheine (1.85 g, 2.37 mmol) dissolved in tetrahydrofuran (70 mL) was slowly added. The mixture was stirred for a 2 h while maintaining the temperature below −30° C. The reaction was quenched by addition of water and then dichloromethane was added. Aqueous phase was washed with dichloromethane and diethylether, concentrated under vacuum and passed through cation exchange column (DOWEX 50WX2). Fractions were analyzed by LCMS and those containing the product were pooled and concentrated under vacuum. 4'-phosphopanetheine was precipitated with addition of Ca(OH)₂ as a calcium salt (332 mg, 0.838 mmol, 35%). The structure of the product was confirmed by comparison of NMR data with the literature [Lee, C—H. et al., J. Am. Chem. Soc. 1975, 1225-1236] and by HRMS. $^1$H NMR (300 MHz, D₂O) δ 0.86 (s, 3H), 1.08 (s, 3H), 2.54 (t, J=6.3 Hz, 2H), 2.87 (t, J=6.3 Hz, 2H), 3.43 (dd, J=10.3, 5.0 Hz, 1H), 3.54 (m, 4H), 3.76 (dd, J=10.3, 6.5 Hz, 1H), 4.14 (s, 1H). The HRMS mass for C₁₁H₂₂N₂O₇SP [M−H]⁻ was found to be 357.0880, which corresponds to the expected mass of 357.0885.

Example 5. Method for Preparation of bis(pivaloyloxymethyl) ester of S-acyl-4'-phosphopantetheine (Corresponds to Example 8 of WO2015/063177)

Preparation of Phosphorylating Reagent

Bis(POM) chloro phosphate for the phosphorylation of S-acetil-pantetheine was prepared according to the published literature (Hwang Y et al., Organic Letters. 2004, 6, 1555; Ruda, G F et al., ChemMedChem. 2007, 2, 1169).

Preparation of Tris(POM) Phosphate

To a solution of trimethyl phosphate (7.01 g, 50 mmol) in dry CH₃CN (42 mL) were sequentially added chloromethylpivalate (29.35 g, 195 mmol) and NaI (22.52 g, 150 mmol). The reaction mixture was heated at reflux (80° C.) for 72 hours, cooled to ambient temperature and diluted with Et₂O (400 mL). The organic phase was washed with water (2×100 ml), saturated Na₂S₂O₃ solution (2×100 mL), dried over Na₂SO₄ and concentrated. Purification on silica gel eluting with hexane/EtOAc 4:1 afforded viscous yellow oil (14.6 g, 66%): $^1$H NMR (300 MHz, CDCl₃) δ 5.66 (d, J=13.7 Hz, 6H), 1.24 (s, 27H) ppm; $^{31}$P NMR (120 MHz, CDCl₃) δ −4.74 (s) ppm; HRMS (M+H⁺) calculated for C₁₈H₃₄O₁₀P 441.1890, found 441.1901.

Preparation of Bis(POM) Hydrogen Phosphate

Tris(POM) phosphate (1 g, 2.3 mmol) was dissolved in piperidine (7 mL) and stirred at room temperature for 12 h.

The solution was concentrated and further evaporated in vacuo until constant weight. (935 mg, 99.0% yield). The crude oil (935 mg, 2.28 mmol) was dissolved in water (20 ml) and treated with Dowex W50X2 H form resin (19.2 g, 11.4 mmol, 0.6 mmol/g). The suspension was stirred at ambient temperature for 1 hour. The resin was filtered and washed with water. The filtrate was concentrated and dried in vacuo affording a white solid (613 mg, 82% yield): $^1$H NMR (300 MHz, CDCl$_3$) δ 8.45 (bs, 1H), 5.62 (d, J=13.2 Hz, 4H), 1.23 (s, 18H) ppm; $^{31}$P NMR (120 MHz, CDCl$_3$) δ −3.17 (s) ppm.

Preparation of Bis(POM) Chloro Phosphate

A solution of bis(POM) hydrogen phosphate (613 mg, 1.88 mmol) and DMF (7.3 µL, 0.094 mmol) in DCM (7.5 mL) was added dropwise to a stirred solution of oxalyl chloride (889 µL, 9.38 mmol) in DCM (7.5 mL) under argon at ambient temperature. Reaction mixture was stirred for 2 hours. The solvent was evaporated under argon to provide a crude yellow oil (671 mg, 1.86 mmol) which was directly used in the next step.

Preparation of S-acetil phosphopantetheine bis[(pivaloyloxy)methyl] ester S-acetyl-pantetheine was prepared as described in [E. Walton et al., J. Am. Chem. Soc. 1954, 76, 1146]. To a stirred solution of S-acetil-pantetheine (463 mg, 1.45 mmol), N,N-iisopropylethylamine (308 µL, 1.77 mmol) and 4-Dimethylaminopyridine (10.9 mg, 0.09 mmol) in 10 ml of DCM at 0° C., was added dropwise under argon a solution of bis(POM) chloro phosphate (590 mg, 1.88 mmol) in 10 ml of DCM. Reaction mixture was allowed to warm to room temperature and stirred for 12 hours. The reaction was quenched with water (10 ml) and extracted with DCM (2×20 ml). Organic phase was washed with saturated solution of NH$_4$Cl, dried over Na$_2$SO$_4$ and concentrated under reduced pressure. Purification on silica gel eluting with DCM/MeOH, 92:8 afforded the product as a yellow oil (401 mg, 44% yield): $^1$H NMR (300 MHz, CDCl$_3$) δ 7.25 (app t, J=6.2 Hz, 1H), 6.39 (app t, J=5.3 Hz, 1H), 5.61-5.71 (m, 4H), 4.13 (dd, J=10.0, 6.9 Hz, 1H), 4.08 (d, J=6.3 Hz, 1H), 3.97 (d, J=5.8 Hz, 1H), 3.75 (dd, J=10.0, 7.2 Hz, 1H), 3.51-3.63 (m, 2H), 3.34-3.50 (m, 2H), 2.95-3.09 (m, 2H), 2.39-2.47 (m, 2H), 2.35 (s, 3H), 1.242 (s, 9H), 1.240 (s, 9H), 1.12 (s, 3H), 0.88 (s, 3H) ppm; $^{31}$P NMR (120 MHz, CDCl$_3$) δ −2.64 (s) ppm.

The invention claimed is:

1. A pharmaceutical composition comprising a phosphopantetheine compound or a pharmaceutically acceptable salt or solvate thereof and an HMG-CoA reductase inhibitor, wherein the phosphopantetheine compound has the structural formula:

(Structure I)

wherein:

Ra is

R$_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —C=NR$_{11}$, —CN, —OR$_{11}$, —OC(O)R$_{11}$, —NR$_{11}$R$_{12}$, —NR$_{11}$C(O)R$_{12}$, —NO$_2$, —N=CR$_{11}$R$_{12}$ or -halogen;

R$_2$ and R$_3$ are independently selected from the group consisting of: —H, -methyl, -ethyl, -phenyl, acetoxymethyl (AM), pivaloyloxymethyl (POM), or R$_2$ and R$_3$ jointly form a structure selected from the group consisting of:

wherein
R$_4$ is —H or -alkyl;
R$_5$ is —H or -alkyl;
R$_6$ is —H, -alkyl, or —CH$_2$(CO)OCH$_3$;
R$_7$ is —H, -alkyl, or -halogen;
R$_8$ is —H or -alkyl;
R$_9$ is —H or -alkyl;
R$_{10}$ is —H or -alkyl;
R$_{11}$ and R$_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen.

2. The composition of claim 1, wherein said HMG-CoA reductase inhibitor is selected from the group consisting of lovastatin, simvastatin, pravastatin, fluvastatin, atorvastatin, cerivastatin, mevastatin, rosuvastatin and the pharmaceutically acceptable lactones, open acids, salts, and esters thereof, and mixtures thereof.

3. The composition of claim 1, wherein R$_2$ and R$_3$ are identical residues.

4. The composition of claim 1, wherein R$_2$ and R$_3$ are each H.

5. The composition of claim 1, wherein R$_1$ is methyl.

6. The composition of claim 1, wherein R$_1$ is methyl, and R$_2$ and R$_3$ are each H.

7. The composition of claim 6, wherein the phosphopantetheine compound is a D stereoisomer.

8. The composition of claim 7, wherein the pharmaceutically acceptable salt or solvate of the phosphopantetheine compound is a calcium salt.

9. A kit comprising:
a first pharmaceutical composition comprising an effective amount of a HMG-CoA reductase inhibitor, and
a second pharmaceutical composition comprising an effective amount of a phosphopantetheine compound or a pharmaceutically acceptable salt or solvate thereof, wherein the phosphopantetheine compound has the chemical formula:

(Structure I)

wherein:
Ra is wherein:
R$_1$ is —H, unsubstituted or substituted alkyl, unsubstituted or substituted alkenyl, substituted or unsubstituted cycloalkyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —C=NR$_{11}$, —CN, —OR$_{11}$, —OC(O)R$_{11}$, —NR$_{11}$R$_{12}$, —NR$_{11}$C(O)R$_{12}$, —NO$_2$, —N=CR$_{11}$R$_{12}$ or -halogen;
R$_2$ and R$_3$ are independently selected from the group consisting of: —H, -methyl, -ethyl, -phenyl, acetoxymethyl (AM), pivaloyloxymethyl (POM), or
R$_2$ and R$_3$ jointly form a structure selected from the group consisting of:

wherein
R$_4$ is —H or -alkyl;
R$_5$ is —H or -alkyl;
R$_6$ is —H, -alkyl, or —CH$_2$(CO)OCH$_3$;
R$_7$ is —H, -alkyl, or -halogen;
R$_8$ is —H or -alkyl;
R$_9$ is —H or -alkyl;
R$_{10}$ is —H or -alkyl;
R$_{11}$ and R$_{12}$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen.

10. The kit of claim 9, wherein said HMG-CoA reductase inhibitor is selected from the group consisting of lovastatin, simvastatin, pravastatin, fluvastatin, atorvastatin, cerivastatin, mevastatin, rosuvastatin and the pharmaceutically acceptable lactones, open acids, salts, and esters thereof, and mixtures thereof.

11. The kit of claim 9, wherein $R_2$ and $R_3$ are identical residues.

12. The kit of claim 9, wherein $R_2$ and $R_3$ are each H.

13. The kit of claim 9, wherein $R_1$ is methyl.

14. The kit of claim 9, wherein $R_1$ is methyl, and $R_2$ and $R_3$ are each H.

15. The kit of claim 14, wherein the phosphopantetheine compound is a D stereoisomer.

16. The kit of claim 15, wherein the pharmaceutically acceptable salt or solvate of the phosphopantetheine compound is a calcium salt.

17. The composition of claim 1 for treating or preventing dyslipidemia, hyperlipidemia, elevated blood cholesterol, elevated blood triglycerides, combined hyperlipidemia, artherosclerosis, cardiovascular disease, heart attack, or stroke.

18. The kit of claim 9 for treating or preventing dyslipidemia, hyperlipidemia, elevated blood cholesterol, elevated blood triglycerides, combined hyperlipidemia, artherosclerosis, cardiovascular disease, heart attack, or stroke.

* * * * *